United States Patent
Qiu et al.

(10) Patent No.: US 12,415,768 B2
(45) Date of Patent: Sep. 16, 2025

(54) METHOD FOR IMPROVING ULTRA-VIOLET LIGHT TRANSMITTANCE OF ETHYLENE GLYCOL

(71) Applicant: SHENZHEN CAPCHEM TECHNOLOGY CO., LTD., Shenzhen (CN)

(72) Inventors: Wenhao Qiu, Shenzhen (CN); Yang Guo, Shenzhen (CN); Bangying Wang, Shenzhen (CN); Shuhua Zeng, Shenzhen (CN)

(73) Assignee: SHENZHEN CAPCHEM TECHNOLOGY CO., LTD., Shenzhen (CN)

( * ) Notice: Subject to any disclaimer, the term of this patent is extended or adjusted under 35 U.S.C. 154(b) by 483 days.

(21) Appl. No.: 18/078,107

(22) Filed: Dec. 9, 2022

(65) Prior Publication Data
US 2023/0406796 A1    Dec. 21, 2023

Related U.S. Application Data

(63) Continuation of application No. PCT/CN2022/123774, filed on Oct. 8, 2022.

(30) Foreign Application Priority Data

Jun. 21, 2022    (CN) .......................... 202210706301.0

(51) Int. Cl.
*C07C 29/94*    (2006.01)
(52) U.S. Cl.
CPC .......... *C07C 29/94* (2013.01); *C07C 2523/02* (2013.01); *C07C 2523/04* (2013.01)

(58) Field of Classification Search
None
See application file for complete search history.

(56) References Cited

FOREIGN PATENT DOCUMENTS

| | | | | |
|---|---|---|---|---|
| CN | 101928201 A | | 12/2010 | |
| CN | 110642676 | * | 1/2020 | ............ C07C 31/22 |
| CN | 110642676 A | | 1/2020 | |
| CN | 114988984 A | | 9/2022 | |
| JP | 2001031606 A | | 2/2001 | |
| JP | 2011068699 | * | 4/2011 | ............ C07C 29/80 |
| JP | 2011068699 A | | 4/2011 | |

OTHER PUBLICATIONS

JP-2011068699 machine translation downloaded from Google patents (Jun. 4, 2025).*
CN-110642676 machine translation downloaded from Google patents (Jun. 4, 2025).*

* cited by examiner

*Primary Examiner* — Clinton A Brooks

(57) ABSTRACT

The present invention provides a method for improving ultra-violet light transmittance of ethylene glycol, which includes the following steps: (1) subjecting ethylene glycol, a catalyst and water to a hydrolysis reaction at 120° C.-150° C.; and (2) adding a stabilizer into a product of the hydrolysis reaction, then conducting distillation at reduced pressure, and condensing to recover a fraction. The method of the present invention can effectively decompose impurities of carboxyl-, conjugated double bond-, aldehyde and ketone-containing complex organic compounds in the ethylene glycol which affect the ultra-violet light transmittance, obviously improve UV values of the ethylene glycol at 220 nm, 275 nm and 350 nm, give consideration to the requirements of environmental protection and safety and economic benefits, and have a broad application prospect.

9 Claims, No Drawings

METHOD FOR IMPROVING ULTRA-VIOLET LIGHT TRANSMITTANCE OF ETHYLENE GLYCOL

TECHNICAL FIELD

The present invention belongs to the technical field of chemical engineering, and particularly relates to a method for improving ultra-violet light transmittance of ethylene glycol.

BACKGROUND

Ethylene glycol is a very important chemical product with a wide range of uses, which can be used as a raw material of an antifreezing agent and a polyester fiber. The industrial demand of the polyester fiber accounts for more than 40% of the total consumption. As the main raw material of the polyester fiber, ethylene glycol has a special ultra-violet light transmittance (hereinafter referred to as an UV value for short) index. That is, the ultra-violet light transmittance of ethylene glycol is determined respectively at 220 nm, 275 nm and 350 nm when the thickness of a liquid layer is 1 cm. Currently, the UV values of most ethylene glycol products in the market are not up to standard. If the UV value is not up to standard, it will affect the quality of a fiber, thereby affecting the application range of the products. Therefore, it is very important for the use of ethylene glycol as the raw material of the polyester fiber how to remove an impurity from ethylene glycol, improve the ultra-violet light transmittance of ethylene glycol and make it meet the standard of polyester-grade ethylene glycol.

Currently, physical and chemical methods are usually employed to remove the impurity from ethylene glycol, among which the physical methods mainly include methods of adsorption and membrane separation, and the chemical method is mainly a catalytic hydrogenation method. The physical methods have defects such as limited adsorption capacity and a complicated preparation process. There are defects in the catalytic hydrogenation method, such as instability of a fixed bed catalyst carrier in a water phase, high energy consumption, by-products complexity, etc. Currently, there are also methods of improving the ultra-violet light transmittance of ethylene glycol by distillation at reduced pressure after alkali treatment, but new substances that affect the ultra-violet light transmittance will be introduced during processes of these treatments, and what these substances are and how to inhibit their formation are still unclear. In view of this, it is necessary to provide a safe, economical and efficient method to improve the quality of ethylene glycol, especially the ultra-violet light transmittance of ethylene glycol.

SUMMARY

Therefore, an objective of the present invention is to provide a method for improving ultra-violet light transmittance of ethylene glycol, which has the advantages of safety, economy, high efficiency and the like.

In order to achieve the aforementioned objective, the present invention adopts the following technical solutions.

A method for improving ultra-violet light transmittance of ethylene glycol, includes the following steps: (1) subjecting ethylene glycol, a catalyst and water to a hydrolysis reaction at 120° C.-150° C.; and (2) adding a stabilizer into a product of the hydrolysis reaction, then conducting distillation at reduced pressure, and condensing to recover a fraction.

In some embodiments, the catalyst is selected from at least one of an alkali metal hydroxide and an alkaline earth metal hydroxide.

In some preferred embodiments, the catalyst is selected from at least one of potassium hydroxide, sodium hydroxide, lithium hydroxide and calcium hydroxide.

More preferably, the catalyst is selected from potassium hydroxide and sodium hydroxide.

In some embodiments, a temperature for the hydrolysis reaction is 120° C.-130° C. when the catalyst is selected from potassium hydroxide.

In some embodiments, the stabilizer is selected from at least one of sodium thiosulfate, potassium thiosulfate, sodium dithionite and potassium dithionite.

In some embodiments, the ethylene glycol includes at least one of carboxyl-, conjugated double bond-, aldehyde and ketone-containing organic compounds.

In some embodiments, the temperature for the hydrolysis reaction is 140° C.-150° C.

In some embodiments, a time for the hydrolysis reaction is 100 min-120 min.

In some embodiments, the temperature for the distillation at reduced pressure is 120° C.-135° C.

In some embodiments, the pressure of the distillation at reduced pressure is −0.0080 KPa~−0.0100 KPa.

In some preferred embodiments, the pressure of the distillation at reduced pressure is −0.0090 KPa~−0.0100 KPa. Further preferably, the pressure of the distillation at reduced pressure is −0.0096 KPa.

In some embodiments, a mass ratio of the catalyst, stabilizer, water and ethylene glycol is catalyst: stabilizer: water:ethylene glycol=1-3:0.1-0.3:150-200:1000.

In some preferred embodiments, the mass ratio of the catalyst, stabilizer, water and ethylene glycol is catalyst: stabilizer:water:ethylene glycol=1-2:0.1-0.2:150-180:1000.

The present invention provides a method for improving the ultra-violet light transmittance of ethylene glycol, in which firstly ethylene glycol is subjected to the hydrolysis reaction under suitable conditions, and then the product of the hydrolysis reaction is subjected to distillation at reduced pressure in the presence of the stabilizer, so as to obtain polyester-grade ethylene glycol with high purity. According to the inventor's own experience and a lot of research, it is found that ethylene glycol is easy to be oxidized or self-polymerized when the product of the hydrolysis reaction of ethylene glycol is directly distilled at reduced pressure, thereby affecting the quality of the final product. However, the oxidation or self-polymerization of ethylene glycol can be effectively inhibited by adding the stabilizer into the product of the hydrolysis reaction obtained by the present invention and then conducting the distillation at reduced pressure; especially, the stabilizer optimized by the present invention has a better inhibition effect. The method of the present invention can effectively decompose impurities of carboxyl-, conjugated double bond-, aldehyde and ketone-containing complex organic compounds in the ethylene glycol which affect the ultra-violet light transmittance, and can effectively inhibit the formation of other substances which affect the ultra-violet light transmittance, so that the UV values of the prepared ethylene glycol at 220 nm, 275 nm and 350 nm are obviously improved, and the yield of ethylene glycol is high. Moreover, the method gives consideration to environmental protection and safety requirements and economic benefits, and has a broad application prospect.

DETAILED DESCRIPTION OF EMBODIMENTS

The experimental methods in the following examples of the present invention which are not specified with specific conditions are generally carried out according to conventional conditions or according to the conditions recommended by the manufacturer. All kinds of commonly-used chemical reagents used in the examples are commercially available products.

Unless otherwise defined, all technical and scientific terms used in the present invention have the same meanings as those commonly understood by those skilled in the art to which the present invention pertains to. Terms used in the specification of the present invention are only for the purpose of describing specific examples, and are not used for limiting the present invention.

The terms "including", "comprising", "containing" and "having" of the present invention and any variations thereof are intended to cover non-exclusive inclusion. For example, processes, methods, devices, products or apparatuses that include a series of steps are not limited to the listed steps or modules, but optionally further includes steps that are not listed, or optionally includes other steps inherent to these processes, methods, products or apparatuses.

The following description will be made with reference to specific examples.

Example 1

This example provided a method for improving ultra-violet light transmittance of ethylene glycol, which included the following steps:
(1) heat-preservation hydrolysis: 100.21 g of crude ethylene glycol (with a content of 99.01%, UV values of 220 nm: 1.18%, 275 nm: 82.14% and 350 nm: 91.28%), 0.1002 g of a sodium hydroxide solution and 15.0315 g of pure water were added into a heat preservation device for hydrolysis treatment at a temperature of 145° C. for 100 min, so as to obtain a hydrolysis reaction product; and
(2) distillation at reduced pressure: the aforementioned hydrolysis reaction product was added into a rectification device, then 0.01 g of anhydrous sodium thiosulfate was added, in the kettle the temperature was controlled to be 120° C.-135° C. and the pressure was controlled to be −0.0096 KPa, and condensation was conducted to recover a fraction, so as to obtain a finished product with an ethylene glycol content of 99.907% and UV values of: 220 nm: 87.02%, 275 nm: 96.45%, 350 nm: 99.82%. The yield of ethylene glycol was 95.31%, which realized improvement of the quality of ethylene glycol.

Example 2

This example provided a method for improving ultra-violet light transmittance of ethylene glycol, which included the following steps:
(1) 100.30 g of crude ethylene glycol (with a content of 98.98%, an UV value of 220 nm: 5.21%, 275 nm: 84.46% and 350 nm: 90.71%), 0.1003 g of a sodium hydroxide solution and 15.045 g of pure water were added into a heat preservation device for hydrolysis treatment at a temperature of 145° C. for 100 min, so as to obtain a hydrolysis reaction product; and
(2) distillation at reduced pressure: the aforementioned hydrolysis reaction product was added into a rectification device, then 0.011 g of anhydrous sodium thiosulfate was added, in the kettle the temperature was controlled to be 120° C.-135° C. and the pressure was controlled to be −0.0096 KPa, and condensation was conducted to recover a fraction, so as to obtain a finished product with an ethylene glycol content of 99.910% and UV values of: 220 nm: 86.41%, 275 nm: 95.52%, 350 nm: 99.79%. The yield of ethylene glycol was 96.01%, which realized improvement of the quality of ethylene glycol.

Example 3

This example provided a method for improving ultra-violet light transmittance of ethylene glycol, which included the following steps:
(1) heat-preservation hydrolysis: 100.20 g of crude ethylene glycol (with a content of 99.00%, an UV value of 220 nm: 4.11%, 275 nm: 81.44% and 350 nm: 91.63%), 0.1002 g of a sodium hydroxide solution and 15.03 g of pure water were added into a heat preservation device for hydrolysis treatment at a temperature of 125° C. for 120 min, so as to obtain a hydrolysis reaction product; and
(2) distillation at reduced pressure: the aforementioned hydrolysis reaction product was added into a rectification device, then 0.012 g of anhydrous sodium dithionite was added, in the kettle the temperature was controlled to be 120° C.-135° C. and the pressure was controlled to be −0.0096 KPa, and condensation was conducted to recover a fraction, so as to obtain a finished product with an ethylene glycol content of 99.905% and UV values of: 220 nm: 87.01%, 275 nm: 96.30%, 350 nm: 99.85%. The yield of ethylene glycol was 95.61%, which realized improvement of the quality of ethylene glycol.

Comparative Example 1

This comparative example provided a method for improving ultra-violet light transmittance of ethylene glycol. The method was the same as Example 1 except the temperature for the hydrolysis reaction, and specifically included the following steps:
(1) 100.21 g of crude ethylene glycol (with a content of 99.01%, an UV value of 220 nm: 1.18%, 275 nm: 82.14% and 350 nm: 91.28%), 0.1002 g of a sodium hydroxide solution and 15.0315 g of pure water were added into a heat preservation device for hydrolysis treatment at a temperature of 115° C. for 100 min, so as to obtain a hydrolysis reaction product; and
(2) distillation at reduced pressure: the aforementioned hydrolysis reaction product was added into a rectification device, then 0.01 g of anhydrous sodium thiosulfate was added, in the kettle the temperature was controlled to be 120° C.-135° C. and the pressure was controlled to be −0.0096 KPa, and condensation was conducted to recover a fraction, so as to obtain a finished product with an ethylene glycol content of 99.79% and UV values of: 220 nm: 60.23%, 275 nm: 85.32%, 350 nm: 92.60%.

Comparative Example 2

This comparative example provided a method for improving ultra-violet light transmittance of ethylene glycol. The method was the same as Example 1 except the temperature for the hydrolysis reaction, and specifically included the following steps:
(1) heat-preservation hydrolysis: 100.21 g of crude ethylene glycol (with a content of 99.01%, an UV value of 220 nm: 1.18%, 275 nm: 82.14% and 350 nm: 91.28%), 0.1002 g of a sodium hydroxide solution and 15.0315 g of pure water were added into a heat preservation device for hydrolysis treatment at a temperature of 155° C. for 100 min, so as to obtain a hydrolysis reaction product; and (2) distillation at reduced pressure: the aforementioned hydrolysis reaction product was added into a rectification device, then 0.01 g of anhydrous sodium thiosulfate was added, in the kettle the temperature was controlled to be 120° C.-135° C. and the pressure was controlled to be −0.0096 KPa, and condensation was conducted to recover a fraction, so as to obtain a finished product with an ethylene glycol content of 99.65% and UV values of: 220 nm: 50.25%, 275 nm: 60.22%, 350 nm: 75.68%.

Comparative Example 3

This comparative example provided a method for improving ultra-violet light transmittance of ethylene glycol, which was the same as Example 1 except that no stabilizer was added, and specifically included the following steps:

(1) heat-preservation hydrolysis: 100.21 g of crude ethylene glycol (with a content of 99.01%, an UV value of 220 nm: 1.18%, 275 nm: 82.14% and 350 nm: 91.28%), 0.1002 g of a sodium hydroxide solution and 15.0315 g of pure water were added into a heat preservation device for hydrolysis treatment at a temperature of 145° C. for 100 min, so as to obtain a hydrolysis reaction product; and (2) distillation at reduced pressure: the aforementioned hydrolysis reaction product was added into a rectification device, in the kettle the temperature was controlled to be 120° C.-135° C. and the pressure was controlled to be −0.0096 KPa, and condensation was conducted to recover a fraction, so as to obtain a finished product with an ethylene glycol content of 99.70% and UV values of: 220 nm: 2.19%, 275 nm: 40.13%, 350 nm: 50.55%. The yield of ethylene glycol was 90.25%.

Comparative Example 4

This comparative example provided a method for improving ultra-violet light transmittance of ethylene glycol. The method was the same as Example 1 except for the addition time of the stabilizer, and specifically included the following steps:

(1) heat-preservation hydrolysis: 100.21 g of crude ethylene glycol (with a content of 99.01%, an UV value of 220 nm: 1.18%, 275 nm: 82.14% and 350 nm: 91.28%), 0.1002 g of a sodium hydroxide solution, 0.01 g of anhydrous sodium thiosulfate and 15.0315 g of pure water were added into a heat preservation device for hydrolysis treatment at a temperature of 145° C. for 100 min, so as to obtain a hydrolysis reaction product; and (2) distillation at reduced pressure: the aforementioned hydrolysis reaction product was added into a rectification device, in the kettle the temperature was controlled to be 120° C.-135° C. and the pressure was controlled to be −0.0096 KPa, and condensation was conducted to recover a fraction, so as to obtain a finished product with an ethylene glycol content of 99.80% and UV values of: 220 nm: 70.23%, 275 nm: 350 nm: 96.01%. The yield of ethylene glycol was 95.00%.

The aforementioned results showed that the method of the present invention could effectively improve the UV values of ethylene glycol at 220 nm, 275 nm and 350 nm. When the temperature for the hydrolysis reaction was lower than 120° C. (Comparative Example 1), the hydrolysis reaction was incomplete, which led to the residue of impurities and affected the UV values of ethylene glycol at 220 nm, 275 nm and 350 nm. When the temperature for the hydrolysis reaction was higher than 150° C. (Comparative Example 2), ethylene glycol would undergo a self-polymerization reaction under high temperature and alkaline conditions, resulting in the formation of new impurities, which would affect the UV values of ethylene glycol at 220 nm, 275 nm and 350 nm. When the stabilizer was not added into the step of distillation at reduced pressure (Comparative Example 3), ethylene glycol would be oxidized or self-polymerized, thereby generating new impurities of aldehydes and ketones, which would affect the UV values of ethylene glycol at 220 nm, 275 nm and 350 nm. When the stabilizer was firstly added in the hydrolysis step (Comparative Example 4), the hydrolysis reaction process might affect the use effect of the stabilizer and affect the UV values of ethylene glycol at 220 nm, 275 nm and 350 nm.

The technical features of the aforementioned examples can be arbitrarily combined. To simplify the description, we do not describe all possible combinations of the technical features in the aforementioned examples. However, as long as there is no contradiction in the combination of these technical features, it should be considered as the scope stated in this specification.

The examples described above are merely illustrative of several embodiments of the present invention, the description of them is more specific and detailed, but cannot be construed as limiting the scope of the present invention accordingly. It should be noted that, several variations and modifications can be made by those of ordinary skills in the art, under the premise of not departing from the concept of the present invention, and these variations and modifications all fall within the claimed scope of the present invention. Therefore, the claimed scope of the patent of the present invention shall be determined by the appended claims.

The invention claimed is:

1. A method for improving ultra-violet light transmittance of crude ethylene glycol, comprising the following steps: (1) subjecting ethylene glycol, a catalyst and water to a hydrolysis reaction at 120° C.-150° C.; and (2) adding a stabilizer into a product of the hydrolysis reaction, then conducting distillation at reduced pressure, and condensing to recover a fraction; wherein the stabilizer is selected from at least one of sodium thiosulfate, potassium thiosulfate, sodium dithionite and potassium dithionite.

2. The method for improving ultra-violet light transmittance of crude ethylene glycol according to claim 1, wherein the catalyst is selected from at least one of an alkali metal hydroxide and an alkaline earth metal hydroxide.

3. The method for improving ultra-violet light transmittance of crude ethylene glycol according to claim 1, wherein the catalyst is selected from at least one of potassium hydroxide, sodium hydroxide, lithium hydroxide and calcium hydroxide.

4. The method for improving ultra-violet light transmittance of crude ethylene glycol according to claim 3, wherein a temperature for the hydrolysis reaction is 120-130° C. when the catalyst is selected from potassium hydroxide.

5. The method for improving ultra-violet light transmittance of crude ethylene glycol according to claim 1, wherein the crude ethylene glycol comprises at least one of carboxyl-, conjugated double bond-, aldehyde and ketone-containing organic compounds.

6. The method for improving ultra-violet light transmittance of crude ethylene glycol according to claim 1, wherein a time for the hydrolysis reaction is 100 min-120 min.

7. The method for improving ultra-violet light transmittance of crude ethylene glycol according to claim 1, wherein a temperature for the distillation at reduced pressure is 120° C.-135° C.

8. The method for improving ultra-violet light transmittance of crude ethylene glycol according to claim 1, wherein a pressure for the distillation at reduced pressure is −0.0080 KPa~−0.0100 KPa.

9. The method for improving ultra-violet light transmittance of crude ethylene glycol according to claim 1, wherein a mass ratio of the catalyst, stabilizer, water and ethylene glycol is catalyst:stabilizer:water:ethylene glycol=1-3:0.1-0.3:150-200:1000.

* * * * *